United States Patent
Lin et al.

(10) Patent No.: US 8,466,291 B2
(45) Date of Patent: Jun. 18, 2013

(54) 1,5-DIDEOXY-1,5-IMINO-D-GLUCITOL COMPOUNDS

(75) Inventors: Chun-Hung Lin, Taipei (TW); Ching-Wen Ho, Taoyuan County (TW)

(73) Assignee: Academia Sinica, Taipei (TW)

( * ) Notice: Subject to any disclaimer, the term of this patent is extended or adjusted under 35 U.S.C. 154(b) by 557 days.

(21) Appl. No.: 12/609,392

(22) Filed: Oct. 30, 2009

(65) Prior Publication Data

US 2010/0113519 A1     May 6, 2010

Related U.S. Application Data

(60) Provisional application No. 61/109,554, filed on Oct. 30, 2008.

(51) Int. Cl.
*C07D 211/00*     (2006.01)
*A61K 31/445*     (2006.01)

(52) U.S. Cl.
USPC .......................................... 546/242; 514/315

(58) Field of Classification Search
USPC ....................................................... 546/242
See application file for complete search history.

(56) References Cited

U.S. PATENT DOCUMENTS

| | | | |
|---|---|---|---|
| 5,221,746 A | * | 6/1993 | Partis et al. ................... 546/220 |
| 2007/0066543 A1 | | 3/2007 | Mahuran et al. |
| 2007/0197471 A1 | | 8/2007 | Ichikawa |

OTHER PUBLICATIONS

Greimel et al Bioorganic and Medicinal Chemistry Letters 2006, 16, 2067-2070.*
Greimel et al WO 2006-100586—abstract, Sep. 28, 2006.*
Partis et al US 5,310,745—abstract, May 10, 1994.*
Platt et al J. Biol. Chem. 1994, 269, 27108-27114—abstract.*
Roeben et al—DE 4009561—abstract, Sep. 26, 1991.*
Zhao et al Bioorganic and Medicinal Chemistry 2008, 16, 6333-6337—abstract.*

* cited by examiner

*Primary Examiner* — John Mabry
(74) *Attorney, Agent, or Firm* — Wolf, Greenfield & Sacks, P.C.

(57) ABSTRACT

1,5-Dideoxy-1,5-imino-D-glucitol compounds as shown in the specification. Also disclosed is a method of treating a hexosaminidase-associated disease.

9 Claims, No Drawings

```
                      SEQUENCE LISTING

<160> NUMBER OF SEQ ID NOS: 2

<210> SEQ ID NO 1
<211> LENGTH: 39
<212> TYPE: DNA
<213> ORGANISM: Artificial
<220> FEATURE:
<223> OTHER INFORMATION: Oligonucleotide

<400> SEQUENCE: 1
gcccatatga tgaagattaa acgactctac ttactggga                              39

<210> SEQ ID NO 2
<211> LENGTH: 39
<212> TYPE: DNA
<213> ORGANISM: Artificial
<220> FEATURE:
<223> OTHER INFORMATION: Oligonucleotide

<400> SEQUENCE: 2
tcactcgagc tatttgtcca gagtaatcat gaagcggcg                              39
```

1,5-DIDEOXY-1,5-IMINO-D-GLUCITOL COMPOUNDS

RELATED APPLICATION

This application claims priority to U.S. Provisional Application No. 61/109,554, filed on Oct. 30, 2008, the content of which is hereby incorporated by reference in its entirety.

BACKGROUND

N-Acetyl-β-hexosaminidase (HEX), a member of lysosomal hydrolases, catalyzes hydrolysis of terminal, non-reducing N-acetyl-β-D-glucosamine (GlcNAc) and N-acetyl-β-D-galactosamine (GalNAc) residues in glycoproteins, gangliosides, and glycosaminoglycans (GAGs).

HEX, released by chondrocytes into the extracellular compartment, promotes cartilage matrix degradation. Osteoarthritis patients have increased HEX activity in synovial fluid. See Steinberg et al., Biochim. Biophys. Acta 1983 757(1): 47. It has been shown that HEX inhibitors prevent or even reverse cartilage matrix degradation and therefore can be used in treating osteoarthritis. See, e.g., Liu et al. Chem. Biol. 2001, 8, 701-11; and Amorelli et al. Bioorg. Med. Chem. Lett. 2008, 18, 2944-2947.

HEX is also associated to lysosomal storage disorders. For example, Tay-Sachs disease and Sandhoff disease are caused by inherited missense mutations. It has been found that these missense mutations do not affect the active site of the enzyme but, rather, inhibit its ability to obtain or retain its native folding in the endoplasmic reticulum, resulting in accelerated degradation and decreased transport to lysosome. See, e.g., Tropak et al., J Biol Chem. 2004; 279(14):13478-87. HEX inhibitors, acting as pharmacological chaperones by binding to the active site, enhance the HEX stability and increase their transport to lysosome. See Tropak et al., Chem. Biol. 2007; 14(2): 153-64. They can be used to treat Tay-Sachs and possibly Sandhoff diseases.

A major barrier to clinical use of HEX inhibitors is that they may also inhibit O-GlcNAcase, an enzyme sharing a common catalytic mechanism with HEX, thereby causing side effects. See, e.g., Vocadlo et al., J. Biol. Chem. 2005, 280, 25313-25322 and Vocadlo et al., Nat. Struct. Mol. Biol. 2006, 13, 365-71. There remains a great need for discovering a drug that selectively inhibits HEX over O-GlcNAcase.

SUMMARY

This invention is based on the discovery that a number of 1,5-dideoxy-1,5-imino-D-glucitol compounds can bind to HEX B, an isoform of HEX, thereby inhibiting the activity of the enzyme.

In one aspect, this invention relates to a compound of formula (I):

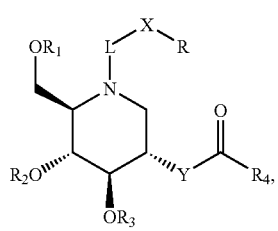

(I)

wherein L is $C_{3-10}$ alkylene, $C_{3-10}$ alkenylene, or $C_{3-10}$ alkynylene; X is —O—, —$NR_a$—, —O—C(O)—, —NR'—C(O)—, —O—S(O)$_2$—, $NR_a$—S(O)$_2$—, or deleted, in which $R_a$ is H, $C_{1-10}$ alkyl, aryl, heteroaryl, $C_{3-8}$ cycloalkyl, or $C_{1-7}$ heterocycloalkyl; R is H, $C_{1-10}$ alkyl, $C_{2-10}$ alkenyl, $C_{2-10}$ alkynyl, aryl, heteroaryl, $C_{3-8}$ cycloalkyl, or $C_{1-7}$ heterocycloalkyl, optionally substituted with $C_{1-10}$ alkyl, aryl, heteroaryl, $C_{3-8}$ cycloalkyl, $C_{1-7}$ heterocycloalkyl, halo, —$N_3$, —CN, nitro, amino, hydroxy, alkoxy, alkylthio, alkylcarbonyl, alkylcarbonyloxy, alkylcarbonylamino, or aminocarbonyl; Y is O or $NR_b$, in which $R_b$ is H, $C_{1-10}$ alkyl, aryl, heteroaryl, $C_{3-8}$ cycloalkyl, or $C_{1-7}$ heterocycloalkyl; each of $R_1$, $R_2$, and $R_3$, independently, is H, $C_{1-10}$ alkyl, aryl, heteroaryl, $C_{3-8}$ cycloalkyl, $C_{1-7}$ heterocycloalkyl, or $COR_c$, in which $R_c$ is $C_{1-10}$ alkyl, aryl, heteroaryl, $C_{3-8}$ cycloalkyl, or $C_{1-7}$ heterocycloalkyl; and $R_4$ is H, —O—($C_1$-$C_{10}$ alkyl), $C_1$-$C_{10}$ alkyl, $C_{2-10}$ alkenyl, $C_{2-10}$ alkynyl aryl, heteroaryl, $C_{3-8}$ cycloalkyl, or $C_{1-7}$ heterocycloalkyl.

Referring to formula (I), the compounds may have one or more of the following features: Y is NH, each of $R_1$, $R_2$, and $R_3$ is H, $R_4$ is $CH_3$, and L is $(CH_2)_6$ or $(CH_2)_7$, X is —NH—, —NH—C(O)—, or deleted; and R is $C_{1-10}$ alkyl, $C_{2-10}$ alkenyl, $C_{2-10}$ alkynyl, aryl, heteroaryl, $C_{3-8}$ cycloalkyl, or $C_{1-7}$ heterocycloalkyl, optionally substituted with $C_{1-10}$ alkyl, aryl, heteroaryl, $C_{3-8}$ cycloalkyl, $C_{1-7}$ heterocycloalkyl, halo, —$N_3$, —CN, nitro, amino, hydroxy, alkoxy, alkylthio, alkylcarbonyl, alkylcarbonyloxy, alkylcarbonylamino, or aminocarbonyl.

Exemplary compounds of formula (I) are shown below:

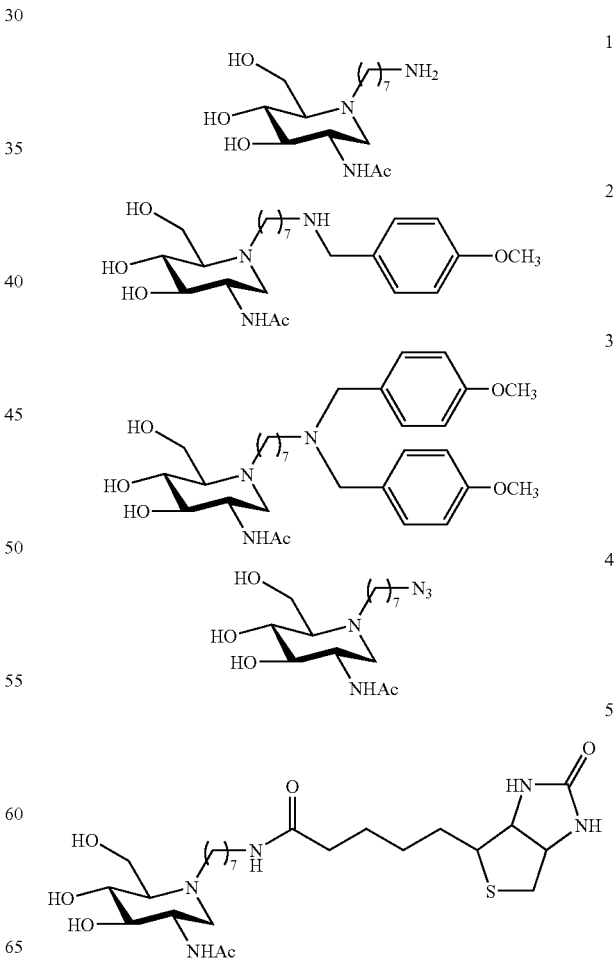

In another aspect, this invention relates to a compound of formula (II):

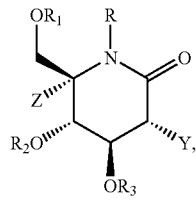

(II)

wherein R is H and Y is $NH_2$; or R is $C_{1-10}$ alkyl, $C_{2-10}$ alkenyl, $C_{2-10}$ alkynyl, aryl, heteroaryl, $C_{3-8}$ cycloalkyl, or $C_{1-7}$ heterocycloalkyl, optionally substituted with $C_{1-10}$ alkyl, aryl, heteroaryl, $C_{3-8}$ cycloalkyl, $C_{1-7}$ heterocycloalkyl, halo, $-N_3$, $-CN$, nitro, amino, hydroxy, alkoxy, alkylthio, alkylcarbonyl, alkylcarbonyloxy, alkylcarbonylamino, or aminocarbonyl; and Y is $OR_a$ or $NR_aR_b$, in which each of $R_a$ and $R_b$, independently, is $C_{1-10}$ alkyl, aryl, heteroaryl, $C_{3-8}$ cycloalkyl, $C_{1-7}$ heterocycloalkyl, $-C(O)-O-(C_1-C_{10}$ alkyl), $-C(O)-(C_1-C_{10}$ alkyl), or $C_1-C_{10}$ alkyl; Z is H, OH, or alkoxy; each of $R_1$, $R_2$ and $R_3$, independently, is H, $C_{1-10}$ alkyl, aryl, heteroaryl, $C_{3-8}$ cycloalkyl, $C_{1-7}$ heterocycloalkyl, or $COR_c$, in which $R_c$ is $C_{1-10}$ alkyl, aryl, heteroaryl, $C_{3-8}$ cycloalkyl, or $C_{1-7}$ heterocycloalkyl.

Referring to formula (II), the above compounds may have one or more of the following features: R is H and Y is $NH_2$; R is $C_{1-10}$ alkyl or $C_{2-10}$ alkynyl, optionally substituted with heteroaryl or amino and Y is $-NHC(O)CH_3$; each of $R_1$, $R_2$, and $R_3$ is H; and Z is H or OH.

Exemplary compounds of formula (II) are shown below:

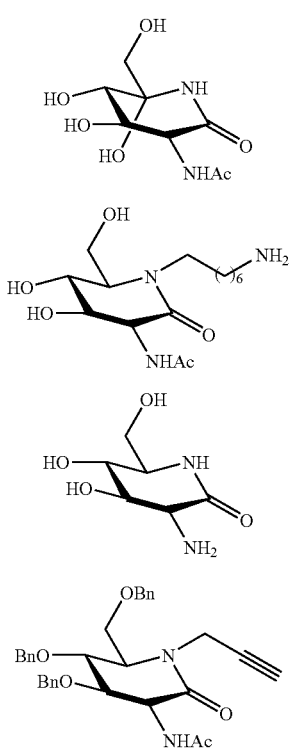

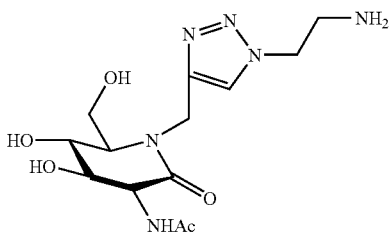

The term "alkyl" refers to a saturated or unsaturated, straight or branched hydrocarbon moiety, such as $-CH_3$ or branched $-C_3H_7$. The term "alkenyl" refers to a saturated or unsaturated, straight or branched hydrocarbon moiety having at least one double bond, such as $-CH_2-CH=CH_2$. The term "alkynyl" refers to a saturated or unsaturated, straight or branched hydrocarbon moiety having at least one triple bond, such as $-CH_3$, $-CH_2-C\equiv CH$. The term "alkylene" refers to a divalent, saturated or unsaturated, linear or branched hydrocarbon moiety, such as $-CH_2-$, $-CH_2CH_2-$, or $-CH_2CH_2CH_2-$. The term "alkenylene" refers to a divalent, saturated or unsaturated, linear or branched hydrocarbon moiety having at least one double bond, such as $-CH_2CH=CH-$. The term "alkynylene" refers to a divalent, saturated or unsaturated, linear or branched hydrocarbon moiety having at least one triple bond, such as $-CH_2C\equiv C-$. The term "cycloalkyl" refers to a saturated or unsaturated, non-aromatic, cyclic hydrocarbon moiety, such as cyclohexyl or cyclohexen-3-yl. The term "heterocycloalkyl" refers to a saturated or unsaturated, non-aromatic, cyclic moiety having at least one ring heteroatom (e.g., N, O, or S), such as 4-tetrahydropyranyl or 4-pyranyl. The term "aryl" refers to a hydrocarbon moiety having one or more aromatic rings. Examples of aryl moieties include phenyl (Ph), naphthyl, pyrenyl, anthryl, and phenanthryl. The term "heteroaryl" refers to a moiety having one or more aromatic rings that contain at least one ring heteroatom (e.g., N, O, or S). Examples of heteroaryl moieties include furyl, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, alkylene, alkenylene, alkynylene, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, arylene, arylalkylene, and heteroaryl include, but are not limited to, $C_1-C_{10}$ alkyl, $C_2-C_{10}$ alkenyl, $C_2-C_{10}$ alkynyl, $C_3-C_8$ cycloalkyl, $C_5-C_8$ cycloalkenyl, $C_1-C_{10}$ alkoxy, aryl, aryloxy, heteroaryl, heteroaryloxy, amino, $C_1-C_{10}$ alkylamino, $C_1-C_{20}$ dialkylamino, arylamino, diarylamino, hydroxyl, halogen, thio, $C_1-C_{10}$ alkylthio, arylthio, alkylsulfonyl, arylsulfonyl, acylamino, aminoacyl, aminothioacyl, amidino, guanidine, ureido, cyano, nitro, acyl, thioacyl, acyloxy, carboxyl, and carboxylic ester. On the other hand, possible substituents on alkyl and alkynyl include all of the above-recited substituents except $C_1-C_{10}$ alkyl, $C_2-C_{10}$ alkenyl, and $C_2-C_{10}$ alkynyl. Cycloalkyl, heterocycloalkyl, aryl, and heteroaryl can also be fused with each other.

In another aspect, this invention relates to a method of inhibiting activity of hexosaminidase and treating a hexosaminidase-associated disease, e.g., osteoarthritis, Tay Sachs disease, or Sandhoff disease. The method includes administering to a subject in need thereof an effective amount of a compound of formula (I) or (II).

The compounds described above include the compounds themselves, as well as their salts, prodrugs, and solvates, if applicable. A salt, for example, can be formed between an anion and a positively charged group (e.g., amino) on a compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a compound. Suitable cations include sodium ion, potassium ion, magnesium ion, calcium ion, and an ammonium cation such as tetramethylammonium ion. The compounds described above also include those salts containing quaternary nitrogen atoms. Examples of prodrugs include esters and other pharmaceutically acceptable derivatives, which, upon administration to a subject, are capable of providing active compounds. A solvate refers to a complex formed between an active compound and a pharmaceutically acceptable solvent. Examples of pharmaceutically acceptable solvents include water, ethanol, isopropanol, ethyl acetate, acetic acid, and ethanolamine.

Also within the scope of this invention is a pharmaceutical composition containing one or more of the compounds described above for use in treating a hexosaminidase-associated disease and the use of such a composition for manufacture of a medicament for the just-mentioned treatment.

The details of one or more embodiments of the invention are set forth in the description below. Other features, objects, and advantages of the invention will be apparent from the description and from the claims.

DETAILED DESCRIPTION

The compounds of this invention can be prepared by methods well known in the art. Scheme 1 shown below illustrates a synthetic route to exemplary Compound 1, a compound of formula (I). Of note, the synthesis of Compound vii from Compound i is described in Graneir et al., *Helv. Chim. Acta.* 1998, 81: 865-880. Via simple nucleophilic substitution, Compound vii can be transformed to Compound viii, deprotection of which affords Compound 1.

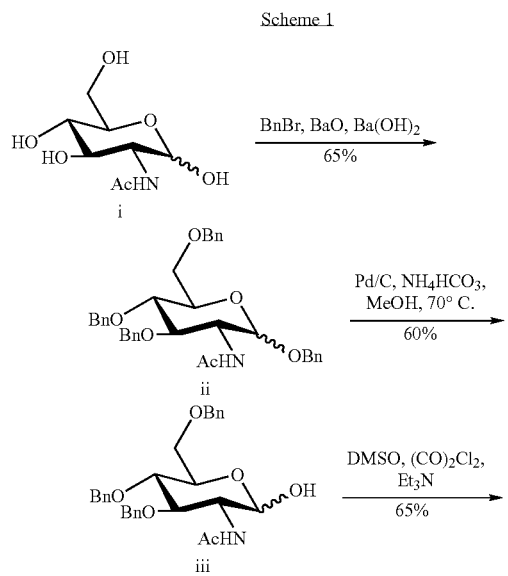

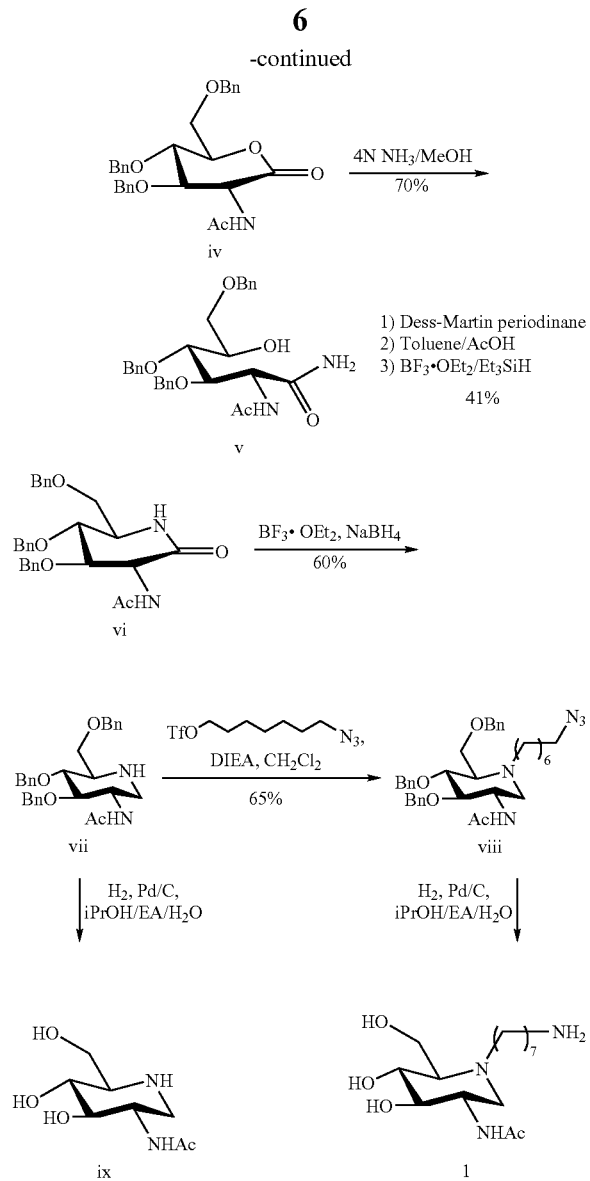

The above scheme is to be construed as illustrative. One can synthesize other compounds of this invention by modifying the process and/or product. For example, as shown in Scheme 2 below, one can react primary amine Compound (a) with an aldehyde compound via reductive amination to form secondary or tertiary amine Compound (b) or (b') or react Compound (a) with an acid compound via amidation to formamide Compound (c). Note that Compound (a) itself can be prepared by methods similar to those shown in the above scheme.

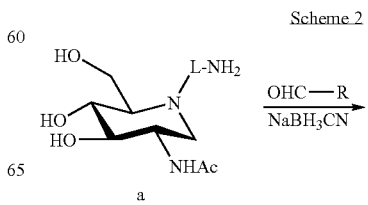

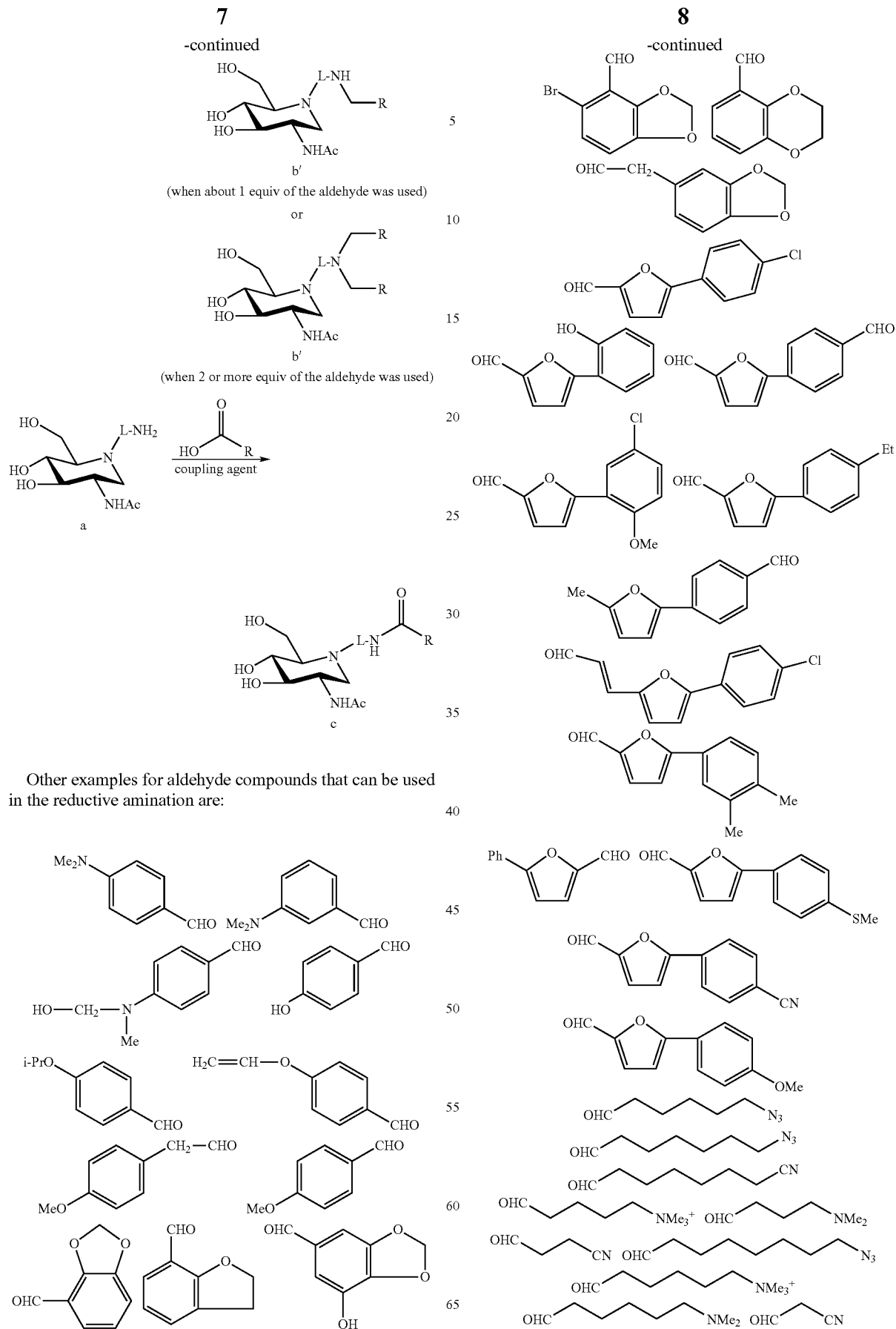
Other examples for aldehyde compounds that can be used in the reductive amination are:

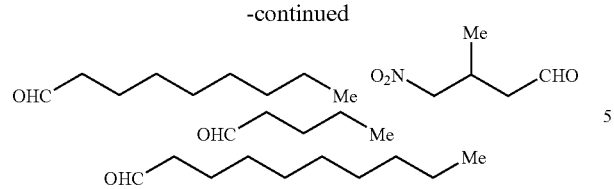
Other examples for acid compounds that can be used in the amidation are:

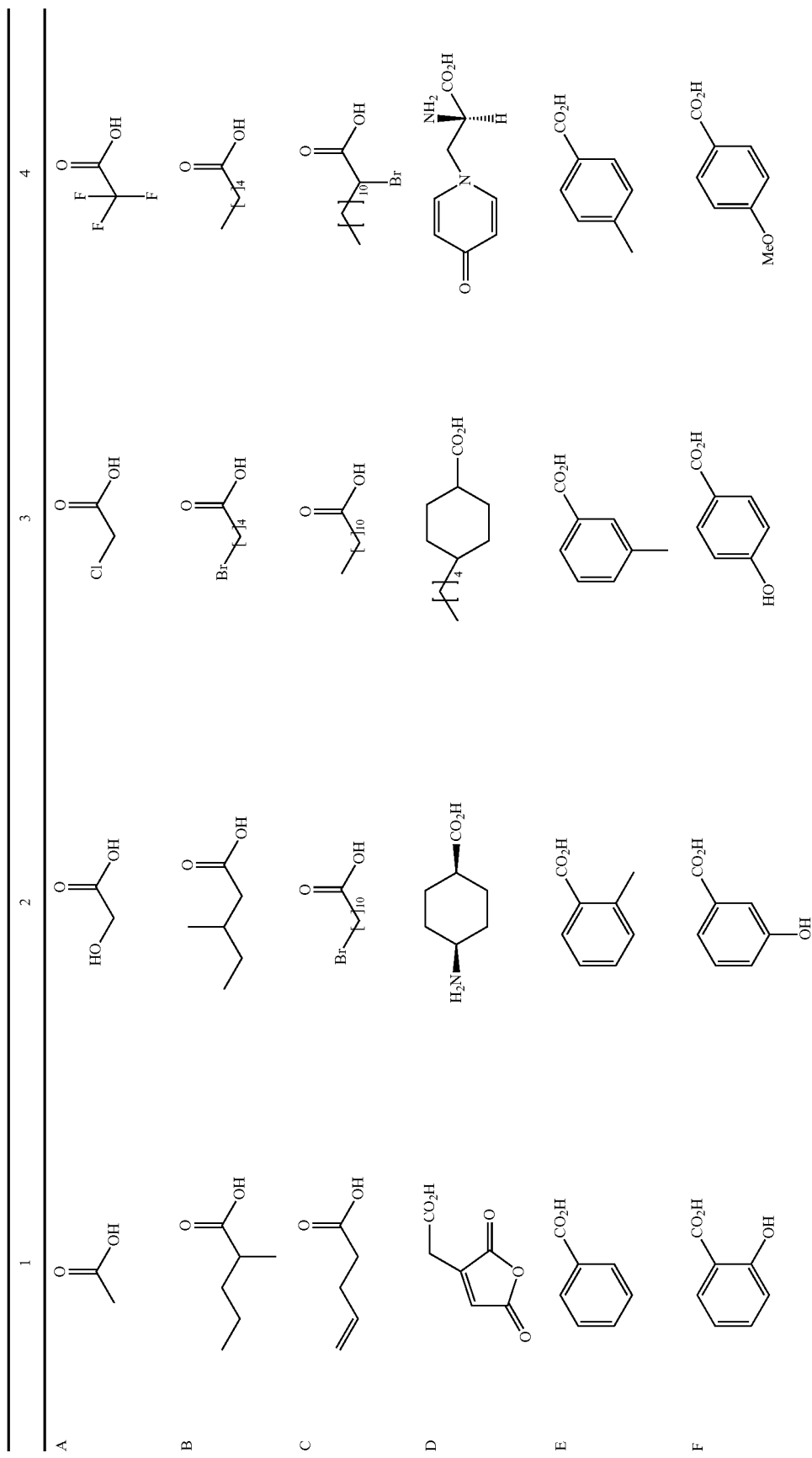

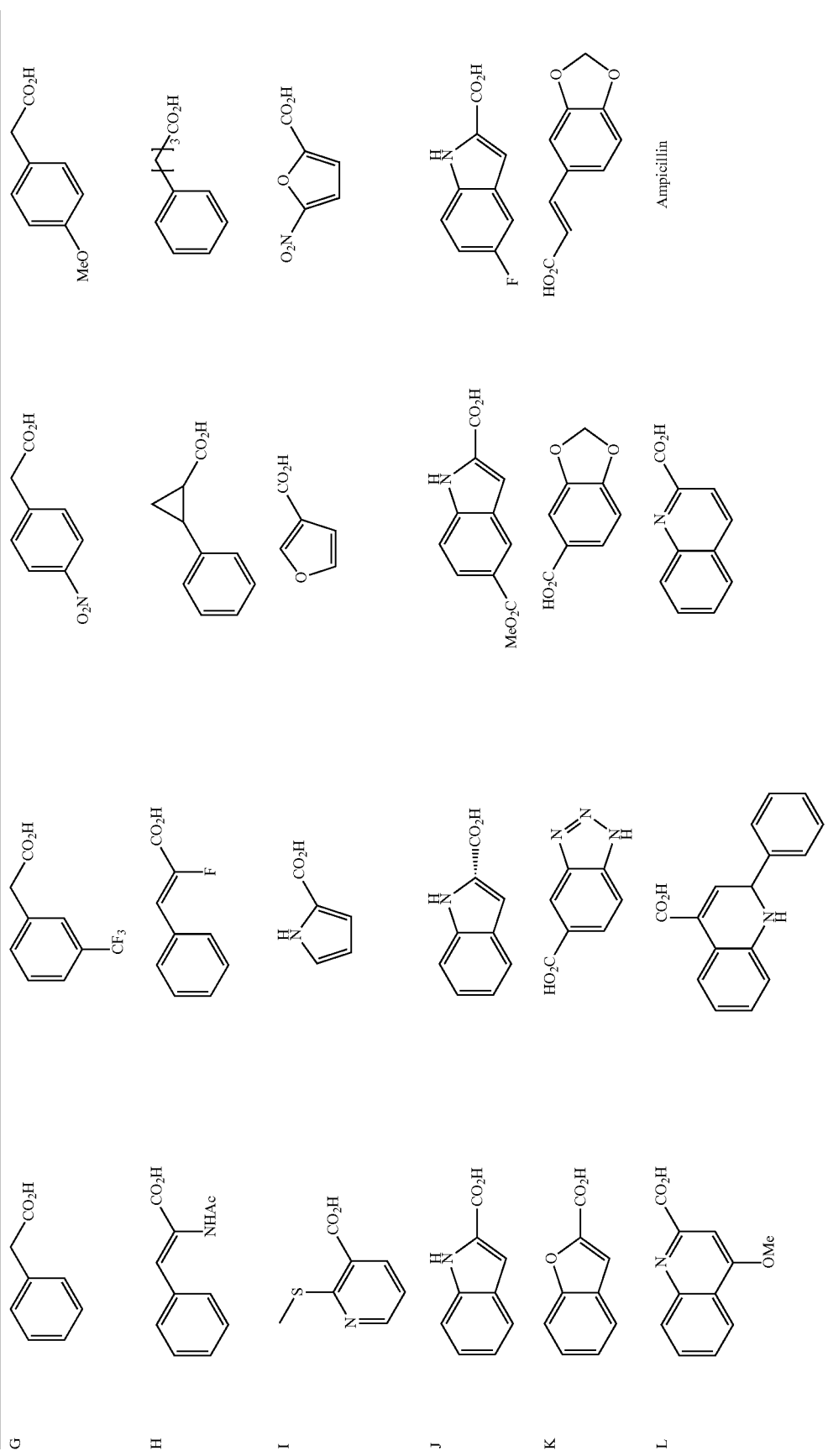

-continued

-continued
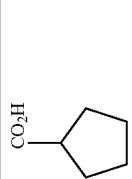 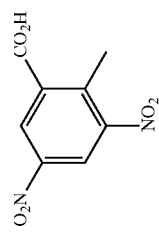 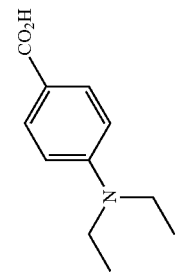 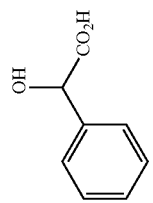 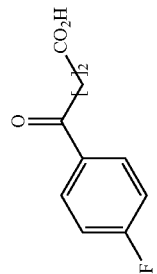

-continued

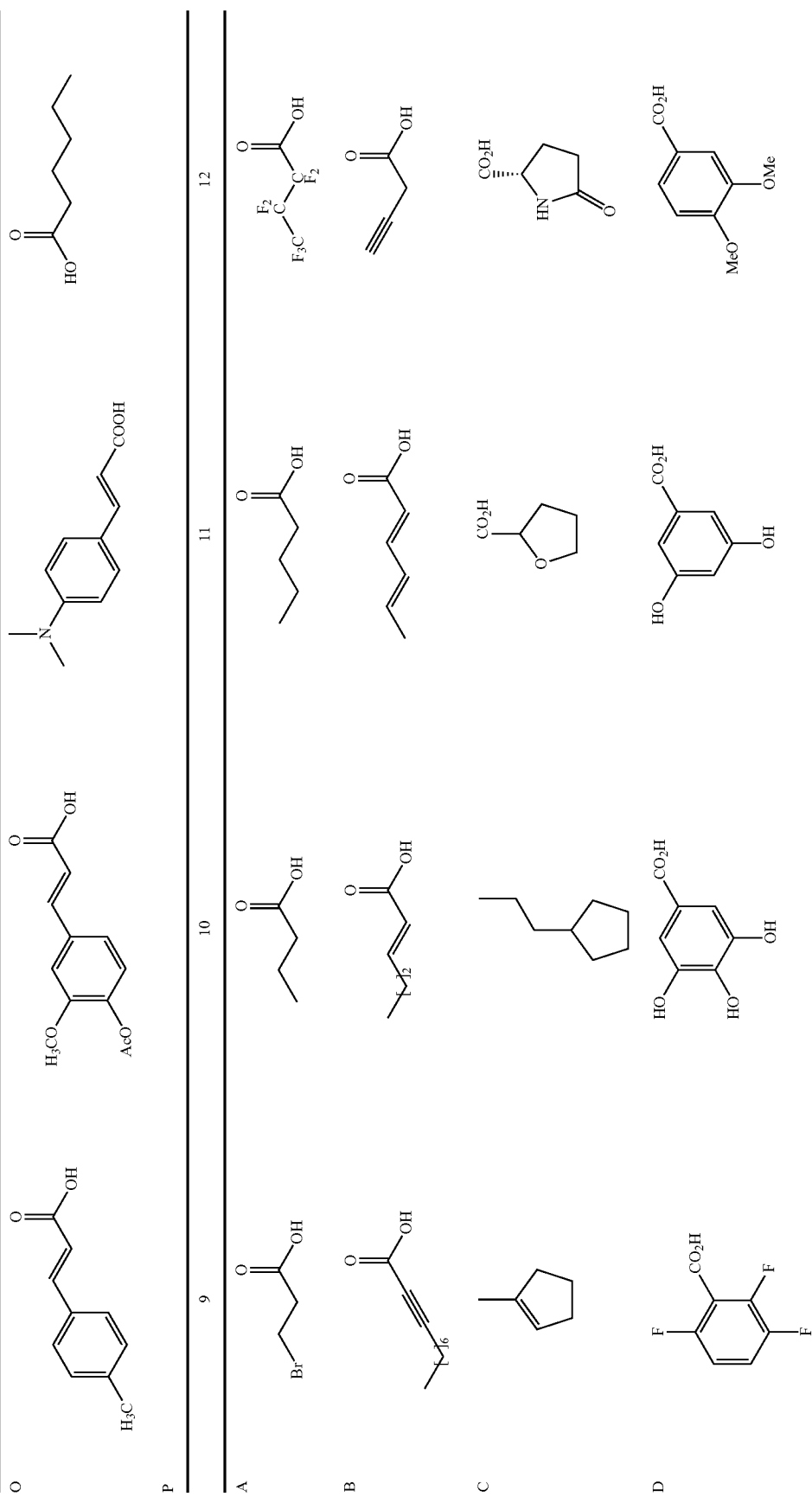

-continued
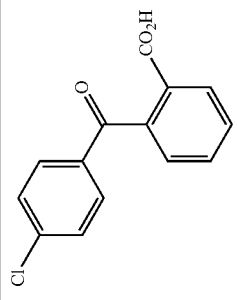 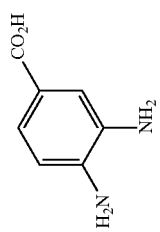 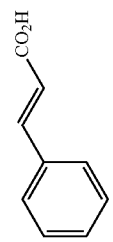 BLANK 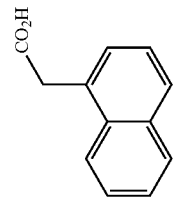
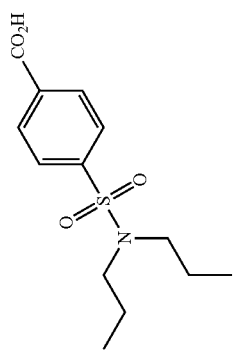 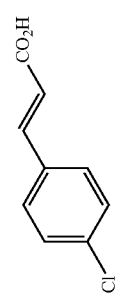 CORE -continued
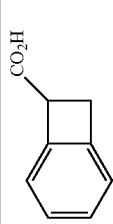
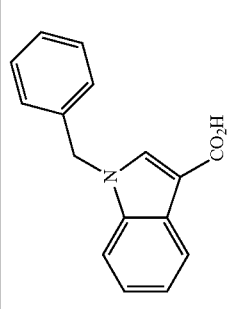
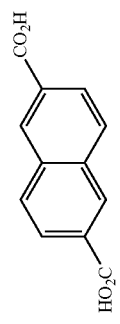
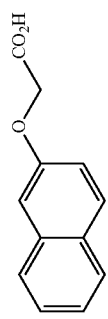
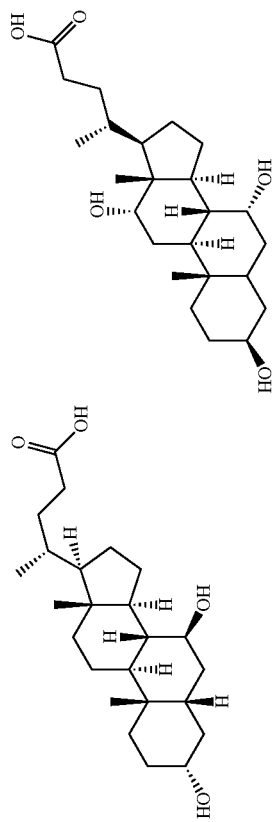
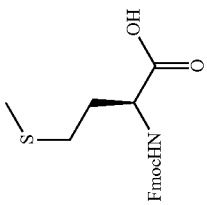
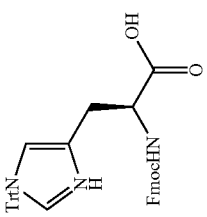
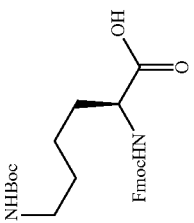
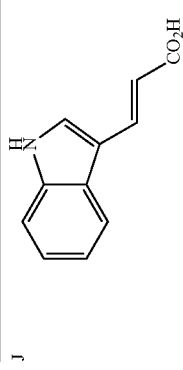
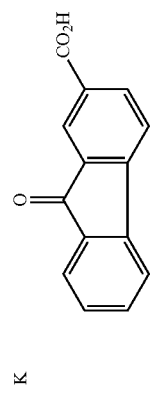
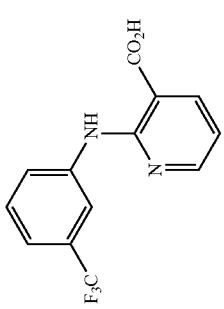
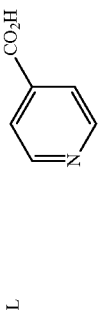
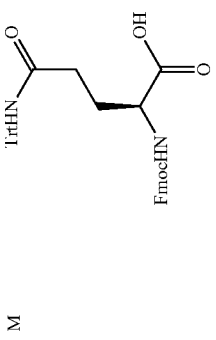
J
K
L
M

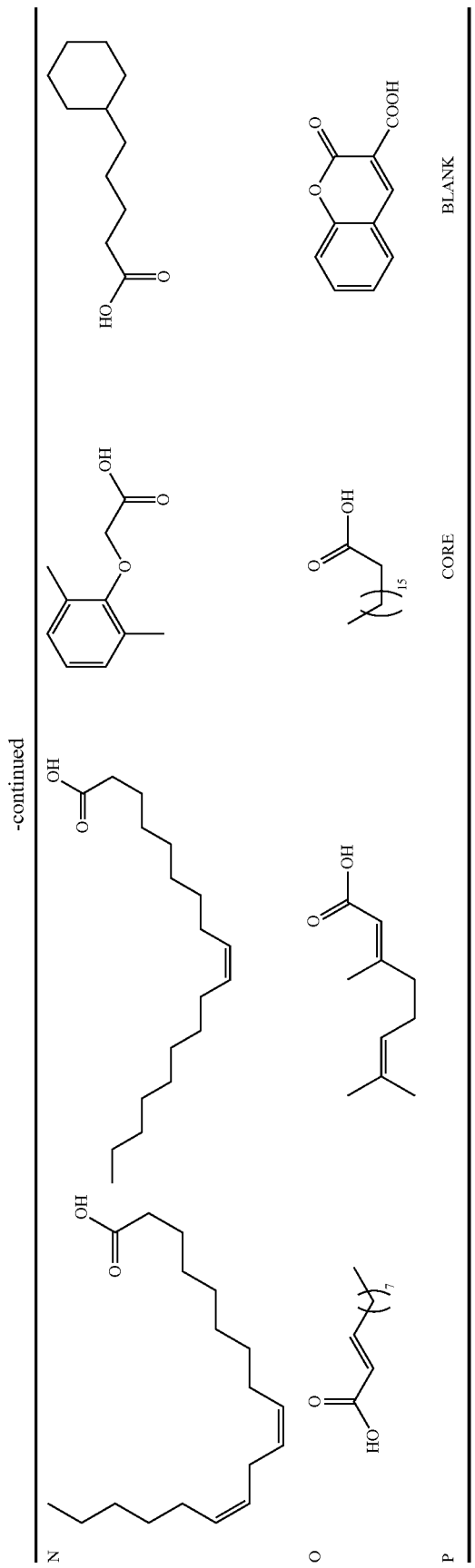

The compounds of formula (II) can be prepared by modifying Compound vi shown in Scheme 1 above via simple chemical transformations.

Synthetic chemistry transformations and protecting group methodologies (protection and deprotection) useful in synthesizing applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Compounds synthesized by the methods described above can be purified by methods well known in the art, e.g., column chromatography, high-pressure liquid chromatography, or recrystallization.

The compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

Examples 1-5 below provides detailed descriptions of the preparation of Compounds 1-5 of this invention.

Also within the scope of this invention is a pharmaceutical composition containing an effective amount of at least one compound described above and a pharmaceutical acceptable carrier. Further, this invention covers a method of administering an effective amount of one or more of the compounds described above to a patient having a hexosaminidase-associated disease. The term "treating" or "treatment" refers to administering one or more compounds described above to a subject, who has a hexosaminidase-associated disease, a symptom of such a disease, or a predisposition toward such a disease, with the purpose to confer a therapeutic effect, e.g., to cure, relieve, alter, affect, ameliorate, or prevent a hexosaminidase-associated disease, the symptom of it, or the predisposition toward it. "An effective amount" refers to the amount of an active compound that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the treatment method of the present invention, a composition having one or more compounds described above can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions. In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having one or more active compounds described above can also be administered in the form of suppositories for rectal administration.

The carrier in the pharmaceutical composition must be "acceptable" in the sense that it is compatible with the active ingredient of the composition (and preferably, capable of stabilizing the active ingredient) and not deleterious to the subject to be treated. One or more solubilizing agents can be utilized as pharmaceutical excipients for delivery of an active compound described above. Examples of other carriers include colloidal silicon oxide, magnesium stearate, cellulose, sodium lauryl sulfate, and D&C Yellow #10.

The compounds described above can be preliminarily screened for their efficacy in treating above-described diseases by an in vitro assay (See Examples 6-8 below) and then confirmed by animal experiments and clinic trials. Computational modeling by, e.g., SYBYL 7.3 program (the Tripos Associates, MO), can also be used to simulate the interaction between a compound and hexosaminidase and predict the compound's activity. Note that SYBYL 7.3 modeling shows that Compound 3 binds to the active site of hexosaminidase. Other methods will also be apparent to those of ordinary skill in the art.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Preparation of N-[1(7-Amino-heptyl)]-2-acetamido-1,2,5-trideoxy-1,5-imino-D-glucitol (Compound 1)

The synthetic route to Compound 1 is shown in Scheme 1 above. Compound vii was prepared according to the methods described in Graneir, T.; Vasella, A. *Helv. Chim. Acta.* 1998, 81, 865-880. The analytical data for this compound is shown below.

$^1$H NMR (400 MHz, CDCl$_3$) δ 7.25-7.40 (m, 15H, Ph), 5.14 (br s, 1H, NH), 4.85 (d, J=12.0 Hz, 1H), 4.81 (d, J=10.9 Hz, 1H), 4.63 (d, J=11.9 Hz, 1H), 4.55 (d, J=10.9 Hz, 1H), 4.50 (d, J=11.8 Hz, 1H), 4.45 (d, J=11.8 Hz, 1H), 3.75-3.79 (m, 1H, H-2), 3.68 (dd, J=9.0, 5.1 Hz, 1H, H-6), 3.62 (dd, J=9.0, 3.0 Hz, 1H, H-6), 3.53 (t, J=8.5 Hz, 1H, H-4), 3.34 (dd, J=9.0, 8.3 Hz, 1H, H-3), 3.30 (dd, J=12.7, 4.2 Hz, 1H, H-1 equa.), 2.74-2.80 (m, 1H, H-5), 2.42 (br s, 1H, NH), 2.32 (dd, J=12.0, 10.6 Hz, 1H, H-1 axial), 1.73 (s, 3H, Ac); $^{13}$C NMR (135 MHz, CDCl$_3$) δ 170.41, 138.37, 137.99, 137.85, 127.87-128.70 (several CH, Aromatic CH), 82.54 (2C), 80.18, 77.48, 74.06, 73.38, 69.08, 59.37, 51.90, 47.63, 23.07; HRMS (FAB) m/z calcd for C$_{29}$H$_{35}$N$_2$O$_4$S (M+H$^+$) 475.2597, found 475.2651.

Compound vii (25 mg, 0.04 mmol) was dissolved in 3 mL of isopropyl alcohol/EtOAc/H$_2$O (2/3/1, volume ratio). Formic acid (25 μL) and 10% Pd/C (25 mg) were added Hydrogen was bubbled into the stirred mixture for 24 h. The reaction mixture was filtered through a pad of celite. The filtrate was evaporated and the dry residue was purified by silica gel column chromatography with CHCl$_3$/MeOH/NH$_4$OH (eluting from 100:0:0 to 60:30:10) to give 8.0 mg of Compound 1v in 74% yield. Mp=220° C.; [α]$^{20}_D$=+ 16.4 (c 1.0, H$_2$O); $^1$H NMR (400 MHz, D$_2$O) δ 3.87-3.94 (m, 1H, H-2), 3.87 (dd, J=12.6, 3.1 Hz, 1H, H-6), 3.75 (dd, J=12.6, 5.2 Hz, 1H, H-6), 3.45-3.53 (m, 2H, H-3, H-4), 3.32 (dd, J=12.4, 4.8 Hz, 1H, H-1 equa.), 2.99-3.03 (m, 1H, H-5), 2.79 (t, J=12.2 Hz, 1H, H-1 axial), 1.92 (s, 3H, Ac); $^{13}$C NMR (135 MHz, D$_2$O) δ 177.29, 76.54, 71.71, 62.71, 60.91, 51.53, 47.29, 24.70; HRMS (FAB) m/z calcd for C$_8$H$_{17}$N$_2$O$_4$ (M+H$^+$) 205.1188, found 205.1218.

To a solution of 7-azido-heptanol (65.0 mg, 0.41 mmol) in anhydrous CH$_2$Cl$_2$ (5 mL) at −50° C. was added pyridine (49.1 mg, 0.62 mmol). After 10 min of stir, the mixture was treated with trifluoromethanesulfonic anhydride (174.92 mg, 0.62 mmol) and stirred for another 45 min. The reaction was quenched by addition of saturated aqueous solution of NaHCO$_3$ and extracted with CH$_2$Cl$_2$. The collected organic layer was washed with brine, dried over MgSO$_4$, filtered and concentrated in vacuo to give 7-azidoheptyl-trifluoromethanesulfonyl ester (127.5 mg) that was used for the next step of alkylation without purification.

To a solution of Compound vii (70.0 mg, 0.15 mmol) in anhydrous CH$_2$Cl$_2$ (5 mL) was added the freshly prepared solution of 7-azido-heptyltrifluoromethanesulfonyl ester (127.5 mg, 0.41 mmol) in CH$_2$Cl$_2$ (4 mL), followed by the dropwise addition of DIEA (53.5 mg, 0.41 mmol). The reaction mixture was stirred at room temperature for 12 h and evaporated in vacuo. The crude residue was purified by silica gel column chromatography with hexane/EtOAc (eluted from 100:0 to 40:60) to give 58.8 mg of product viii in 65.0% yield. [α]$^{20}_D$=+ 6.91 (c 0.0024, MeOH); $^1$H NMR (400 MHz, CD$_3$OD) δ 7.22-7.40 (m, 15H, Aromatic CH), 4.80 (dd, J=11.4, 2.7 Hz, 2H), 4.71 (d, J=11.4 Hz, 1H), 4.58 (d, J=11.0 Hz, 1H), 4.51 (d, J=12.0 Hz, 1H), 4.46 (d, J=12.0 Hz, 1H), 4.12 (ddd, J=11.0, 10.1, 4.3 Hz, 1H, H-2), 3.74 (dd, J=10.6, 3.1 Hz, 1H, H-6), 3.69 (dd, J=10.6, 2.4 Hz, 1H, H-6), 3.60 (dd, J=9.2, 6.6 Hz, 1H, H-3), 3.45 (dd, J=9.2, 8.8 Hz, 1H, H-4), 3.29 (t, J=6.8 Hz, 2H, H-13), 2.99 (dd, J=11.6, 4.4 Hz, 1H, H-1 equa.), 2.71-2.79 (m, 1H, H-11), 2.50-2.60 (m, 2H, H-5, H-11), 2.29 (dd, J=11.0, 10.9 Hz, 1H, H-1 axial), 1.90 (s, 3H, Ac), 1.53-1.60 (m, 2H), 1.42-1.49 (m, 2H), 1.30-1.36 (m, 6H); $^{13}$C NMR (135 MHz, CD$_3$OD) δ 173.08, 140.17, 139.81, 139.32, 129.69 (2C), 129.61 (2C), 129.11 (3C), 128.88 (3C), 128.84 (3C), 128.76 (2C), 85.55, 80.04, 76.04, 75.74, 74.38, 66.73, 65.48, 55.08, 53.60, 52.57, 50.74, 30.11, 29.95, 28.34, 27.90, 25.64, 23.04; HRMS (FAB) m/z calcd for C$_{36}$H$_{48}$N$_5$O$_4$ (M+H$^+$) 614.3706, found 614.3743.

Compound viii was prepared by reacting Compound vii with Tf(CH$_2$)N$_3$ in CH$_2$Cl$_2$ and disiopropylethylamine. Compound viii (50.0 mg, 0.08 mmol) was deprotected by hydrogenolysis as described above to generate 18.4 mg of Compound 1 in 71% yield. [α]$^{20}_D$=+ 1.50 (c 0.12, MeOH); $^1$H NMR (400 MHz, CD$_3$OD) δ 3.89-3.99 (m, 3H, H-6, H-2), 3.52 (dd, J=9.3, 9.1 Hz, 1H, H-4), 3.43 (dd, J=9.9, 9.2 Hz, 1H, H-3), 3.22 (dd, J=11.6, 4.4 Hz, 1H, H-1 equa.), 3.05-3.09 (m, 1H, H-7), 2.96 (t, J=7.5 Hz, 2H, H-13), 2.78-2.84 (m, 1H, H-7), 2.53-2.60 (m, 1H, H-5), 2.51 (dd, J=11.6, 11.1 Hz, 1H, H-1 axial), 2.01 (s, 3H, Ac), 1.60-1.70 (m, 4H), 1.39-1.47 (m, 6H); $^{13}$C NMR (135 MHz, CD$_3$OD) δ 173.88, 76.53, 71.79, 67.78, 58.48, 54.52, 53.49, 51.15, 40.85, 30.69, 28.46, 27.77, 27.15, 25.14, 22.93; HRMS (FAB) m/z calcd for C$_{15}$H$_{32}$N$_3$O$_4$ (M+H$^+$) 318.2393, found 318.2363.

Example 2

Preparation of Compound 2

To a solution of Compound 1 (10.0 mg, 0.032 mmol) in methanol (2 mL) was added 4-methoxybenzaldehyde (5.15 mg, 0.038 mmol). NaBH$_3$CN (6.0 mg, 0.096 mmol) was then added slowly to the solution. The resulting mixture was stirred for 36 h at room temperature. After evaporation to remove the reaction solvent, the residue was purified by silica gel column chromatography with CHCl$_3$/MeOH/NH$_4$OH (6:3.5:0.5) to give 8.2 mg of Compound 2 as a colorless oil in 60% yield. [α]$^{20}_D$=+ 3.00 (c 0.001, MeOH); $^1$H NMR (400 MHz, CD$_3$OD) δ 7.43 (d, J=8.6 Hz, 2H), 7.01 (d, J=8.6 Hz, 2H), 4.14 (s, 2H), 3.88-4.01 (m, 3H, H-6, H-2), 3.83 (s, 3H, —OCH$_3$), 3.52 (t, J=9.4 Hz, 1H, H-3), 3.28-3.40 (m, 2H, H-4, H-1 equa.), 3.10-3.17 (m, 1H, H-7), 3.06 (t, J=7.9 Hz, 2H, H-13), 2.77-2.84 (m, 1H, H 7), 2.41-2.60 (m, 2H, H-5, H-1 axial), 1.99 (s, 3H, Ac), 1.61-1.74 (m, 4H), 1.32-1.45 (m, 6H); $^{13}$C NMR (135 MHz, CD$_3$OD) δ 173.91, 162.35, 132.65 (2C), 124.51, 115.74 (2C), 76.42, 71.53, 67.92, 56.01, 54.36, 53.63, 52.05 (2C), 50.88, 46.78, 29.89, 27.84, 27.52, 27.14, 25.31, 22.86; HRMS (FAB) m/z calcd for C$_{23}$H$_{40}$N$_3$O$_5$ (M+H$^+$) 438.2968, found 438.2958.

Example 3

Preparation of Compound 3

To a solution of Compound 1 (30.0 mg, 0.095 mmol) in methanol was added 4-methoxybenzaldehyde (54.0 mg, 0.38 mmol). NaBH$_3$CN (27.0 mg, 0.39 mmol) was then slowly added to the solution. After stirring at room temperature for 36 h, the reaction mixture was evaporated and purified by silica gel column chromatography with CHCl$_3$/MeOH (3:1) to give 34.2 mg of Compound 3 as a colorless oil in 65% yield. [α]$^{20}_D$=+3.75 (c 0.0016, MeOH); $^1$H NMR (400 MHz, CD$_3$OD) δ 7.27 (d, J=8.5 Hz, 4H), 6.91 (d, J=8.5 Hz, 4H), 3.83-3.88 (m, 3H, H-6, H-2), 3.80 (s, 6H, —OCH$_3$), 3.61 (bs, 4H, N—CH$_2$), 3.42 (t, J=9.1 Hz, 1H, H-3), 3.23 (dd, J=10.0, 9.0 Hz, 1H, H-4), 3.04 (dd, J=11.3, 4.4 Hz, 1H, H-1 equa.), 2.77-2.84 (m, 1H, H-7), 2.47-2.57 (m, 3H, H-7, H-13), 2.10-2.19 (m, 2H, H-5, H-1 axial), 1.98 (s, 3H, Ac), 1.39-1.58 (m, 4H), 1.22-1.32 (m, 6H); $^{13}$C NMR (135 MHz, CD$_3$OD) δ 173.75, 161.31 (2C), 132.43 (4C), 115.22 (4C), 114.91 (2C), 77.57, 72.66, 67.67, 59.55, 58.42 (2C), 55.95 (2C), 55.50, 53.63, 53.48, 51.85, 30.16, 28.41, 28.05, 26.44, 25.65, 22.90; HRMS (FAB) m/z calcd for C$_{31}$H$_{48}$N$_3$O$_6$ (M+H$^+$) 558.3543, found 558.3530.

Example 4

Preparation of Compound 4

Compound 1 (100.0 mg, 0.31 mmol) dissolved in 2 mL of H$_2$O was treated with potassium carbonate (70.0 mg, 0.47 mmol) and CuSO$_4$ hydrate (1.0 mg, 6.28 μmol). To the resulting mixture was added MeOH (4 mL), followed by addition of TfN$_3$ solution (in CH$_2$Cl$_2$). After stirring at room temperature for 24 h, the mixture was evaporated and purified by silica gel column chromatography with CHCl$_3$/MeOH (eluting from 100:0 to 80:20) to give 90 mg of azide 5 in 83% yield. [α]$^{20}_D$=+4.4 (c 0.0018, MeOH); $^1$H NMR (400 MHz, CD$_3$OD) δ 3.89-3.92 (m, 2H, H-6, H-2), 3.86 (dd, J=10.7, 4.3 Hz, 1H, H-6), 3.46 (t, J=9.2 Hz, 1H, H-3), 3.26-3.34 (m, 3H, H-4, H-13), 3.10 (dd, J=11.4, 4.5 Hz, 1H, H-1 equa.), 2.87-2.94 (m, 1H, H-7), 2.63-2.70 (m, 1H, H-7), 2.24-2.31 (m, 2H, H-5, H-1 axial), 2.00 (s, 3H, Ac), 1.51-1.65 (m, 4H), 1.31-1.41 (m, 6H); $^{13}$C NMR (135 MHz, CD$_3$OD) δ 173.84, 77.46, 72.47, 67.45, 59.18, 55.33, 53.68, 52.56, 51.65, 30.16, 29.93, 28.41, 27.85, 25.34, 22.89; HRMS (FAB) m/z calcd for C$_{15}$H$_{30}$N$_5$O$_4$ (M+H$^+$) 334.2298, found 344.2294.

Example 5

Preparation of Compound 5

To a solution of Compound 1 (7.0 mg, 0.022 mmol) in DMF (1.0 mL) was added biotin-N-hydroxysuccinimide ester (9.0 mg, 0.026 mmol) and N,N-diisopropylethylamine (DIEA, 3.36 mg, 0.026 mmol). The reaction mixture was stirred for 12 h, evaporated in vacuo, and purified by flash column chromatography with CHCl$_3$/MeOH (7:3) to give 7.8 mg of product 5 in 65.0% yield. [α]$^{20}_D$=+34.0 (c 0.001, MeOH); $^1$H NMR (400 MHz, CD$_3$OD) δ 4.49-4.53 (m, 1H), 4.30-4.34 (m, 1H), 3.83-3.92 (m, 3H, H-6, H-2), 3.45 (t, J=9.3 Hz, 1H, H-3), 3.18-3.28 (m, 3H), 3.10 (dd, J=11.4, 4.6 Hz, 1H, H-1 equa.), 2.95 (dd, J=11.4, 4.6 Hz, 1H), 2.87-2.91 (m, 1H, H-7), 2.72 (dd, J=12.9, 3.7 Hz, 1H), 2.59-2.68 (m, 1H, H-7), 2.25-2.30 (m, 3H), 2.17-2.24 (m, 2H), 1.98 (s, 3H, Ac), 1.57-1.79 (m, 4H), 1.41-1.53 (m, 6H), 1.29-1.37 (m, 6H); $^{13}$C NMR (135 MHz, CD$_3$OD) δ 176.12, 173.73, 166.25, 77.83, 72.88, 67.58, 63.55, 61.78, 59.89, 57.18, 55.75, 53.65, 52.04, 41.19, 40.48, 36.98, 30.89, 30.49, 29.92, 29.66, 28.62, 28.08, 27.09, 25.66, 22.91; HRMS (FAB) m/z calcd for C$_{25}$H$_{45}$N$_5$O$_6$S (M+H$^+$) 554.3169, found 544.3181.

Example 6

Enzymatic Activity of β-GlcNAcase and Hex B in the Presence or Absence of Compounds 1-5 and Compound ix

*Bacteroids fragilis* O-GlcNAcase, which is highly homologous to human O-GlcNAcase, was prepared as follows. Based on the genome sequence of *B. fragilis* (NCTC 9343) as disclosed in GenBank accession no. CR626927 (Oct. 23, 2008), a DNA fragment encoding the *B. fragilis* O-GlcNAcse was amplified via polymerase chain reaction (PCR), using the primers of: 5'-GCCCATATGATGAAGATTAAACGACTC-TACTTACTGGGA-3' (SEQ ID NO:1) (forward primer) and 5'-TCACTCGAGCTATTTGTCCAGAGTAAT-CATGAAGCGGCG-3' (SEQ ID NO:2) (reverse primer). The PCR product was cloned into pGEM-T Easy vector (Promega) via cloning sites Nde1 and Xho1 and then subcloned into pET21b vector to produce expression plasmid pOGA, which encodes a fusion protein including O-GlcNAcase and a His$_6$ tag at the C-terminus Plasmid pOGA was transformed into *E. coli* BL21 (DE3) cells and a positive transformant was cultured in Luria-Bertani (LB) medium with ampicillin (100 μg/mL) overnight. The *E. coli* culture, transferred to fresh LB medium, was incubated at 37° C. and, when A$_{600}$ of the culture reached 0.6, isopropyl-β-D-thiogalactopyranoside (final conc: 250 μM) was added to induce expression of O-GlcNAcse. The induced cells were further cultured at 16° C. overnight, harvested, and disrupted to produce a cell lysate. Upon centrifugation, the supernatant thus obtained was loaded onto a nickel-affinity column. After elution, a fraction containing O-GlcNAcse was collected and the enzyme contained therein was further purified by gel filtration using a Superdex 6 column. See Dennis et al., *Nat Struct Mol Biol* 2006, 13: 365-71. The purified protein was concentrated using a 10 kDa-cutoff concentrator and dialyzed against 20 mM HEPES (pH 7.5).

Hex B protein (isolated from human placenta) was purchased from Sigma Co.

Both O-GlcNAcase and Hex B were subjected to Michaelis-Menton kinetic analysis to determine the kinetics of their enzymatic activity in the presence of absence of Compounds 1-5 and Compound ix, using 4-methylumbelliferyl-N-acetyl-β-D-glucosaminide (4MU-NAG; purchased from Sigma Co.) as the substrate (a fluorogenic substrate). The reaction conditions for each enzyme are shown below:

O-GlcNAcase: reaction mixture (0.5 nM O-GlcNAcase (200 μL) in 50 mM citric acid, 100 mM NaCl, 0.1% BSA, 0.05-1.5 mM substrate, pH 4.25) was incubated at 30° C. for 25 minutes. The enzyme activity at different time points was determined by measuring the levels of the fluorescent signals (excitation wavelength: 360 nm; emission wavelength: 460 nm) released from 4-methylumbelliferone, a product of the enzyme reaction.

Hex B: reaction mixture (0.1 nM Hex B (200 μL), 50 mM NaH$_2$PO$_4$, 100 mM NaCl, 0.1% BSA, 0.05-1.5 mM substrate, pH 6.5) was incubated at 30° C. for 25 minutes. The reaction was terminated by addition of a 3× quenching buffer (200 mM sodium glycine buffer, pH 10.8). The enzyme activity was determined as described above.

The data thus obtained were fitted into the Michaelis-Menten equation using the KaleidaGraph software to determine the K$_M$ values of both enzymes. The results are shown below:

O-GlcNAcase: K$_M$=269.8±10.4 μM and k$_{cat}$=6.35 s$^{-1}$;
Hex B: K$_m$=97.1±5.2 μM and k$_{cat}$=5.3 s$^{-1}$.

To determine the effects of Compounds 1-5 and Compound ix on the kinetics of both enzymes, the enzyme reactions described above were performed in the presence of each compound at different concentrations. In these reactions, the substrate concentrations were three to five fold of the concentration used for determining K$_M$ (absent compounds) and the ratio between the enzyme and the compound was 0.1-0.5 nM to 0.3 nM-200 uM. The data thus obtained were analyzed by the Lineweaver-Burk plot. The K$_i$ values were determined by the double reciprocal plot (1/V vs. 1/[S]). More specifically, the K$_m$ values for each enzyme in the presence of one of the test compounds first determined and these values were further plotted in view of the concentrations of the compound. K$_i$ was determined by calculating the negative value of the resulting x-intercept. The selectivity of each compound was calculated by the formula: K$_{i\ O\text{-}GlcNAcase}$/K$_{i\ Hex\ B}$.

As shown in Table 1 below, all of Compounds 1-5 and ix were selective in inhibiting HEX over *Bacteroids fragilis* O-GlcNAcase, i.e., having selectivity ratios ranging from 12 to 190,000. Unexpectedly, the selectivity of Compounds 1-5 is much higher than the selectivity of Compound ix.

TABLE 1

Inhibition of Human HEX B and Bacteroids fragilis O-GlcNAcase by Compounds 1-5 and Compound ix.

|    | $K_I$ of O-GlcNAcase ($\mu$M) | $K_I$ of HEX B ($\mu$M) | Selectivity ($K_{I\,O\text{-}GlcNAcase}/K_{I\,HEX}$) |
|----|-------------------------------|--------------------------|------------------------------------------------------|
| ix | 6.7 ± 0.98                    | 0.54 ± 0.25              | 12                                                   |
| 1  | 75.3 ± 9.13                   | 0.0021 ± 0.00038         | 36,000                                               |
| 2  | 72.1 ± 0.88                   | 0.0012 ± 0.00023         | 60,000                                               |
| 3  | 129.0 ± 2.55                  | 0.00069 ± 0.000077       | 190,000                                              |
| 4  | 95.7 ± 8.37                   | 1.7 ± 0.56               | 56                                                   |
| 5  | 69.6 ± 1.77                   | 0.0267 ± 0.00111         | 2,600                                                |

Human O-GlcNAcase was also prepared and tested according to the procedures described in Gao et al., *J. Biol. Chem.* 2001, 276, 9838-9845 and Macauley et al., *J. Am. Chem. Soc.* 2005, 127, 17202-17203. Inhibition constants and selectivities of Compounds 1-5 and ix are shown in Table 2 below. The results indicate that Compounds 1-5 and ix were selective in inhibiting HEX B over human O-GlcNAcase, i.e., having selectivity ratios ranging from 43 to 250,000. Unexpectedly, the selectivity of Compounds 1-5 is much higher than the selectivity of Compound ix.

TABLE 2

Inhibition of Human HEX B and Human O-GlcNAcase by Compounds 1-5 and Compound ix.

|    | $K_I$ of O-GlcNAcase ($\mu$M) | $K_I$ of HEX B ($\mu$M) | Selectivity ($K_{I\,O\text{-}GlcNAcase}/K_{I\,HEX}$) |
|----|-------------------------------|--------------------------|------------------------------------------------------|
| ix | 23.6 ± 0.97                   | 0.54 ± 0.25              | 43                                                   |
| 1  | 107.7 ± 9.17                  | 0.0021 ± 0.00038         | 51,000                                               |
| 2  | 101.5 ± 6.47                  | 0.0012 ± 0.00023         | 85,000                                               |
| 3  | 175.6 ± 2.15                  | 0.00069 ± 0.000077       | 250,000                                              |
| 4  | 155.1 ± 9.87                  | 1.7 ± 0.56               | 91                                                   |
| 5  | 145.0 ± 1.77                  | 0.0267 ± 0.00111         | 5,400                                                |

Additionally, Compounds 1 and 3 were tested to determine their inhibitory effects on O-GlcNAcase in human 293T cells. The cells were treated with 10 $\mu$M Compound 1 or 3 for 16 hours. The level of protein-associated O-GlcNAc moieties in the treated cells was determined by Western blot analysis using an anti-O-GlcNAc antibody. See Macauley et al., *J. Biol. Chem.* 2005, 280, 25313-25322. Two known O-GlcNAcase inhibitors, PUGNAc (10 $\mu$M) and STZ (10 $\mu$M), were used as positive controls (Hanover et al., *Arch Biochem. Biophys.* 1999, 362, 38-45 and Rao et al., *EMBO J.* 2006, 25, 1569-1578). The result shows that the level of O-GlcNAc moieties in compound 1 or 3-treated cells were not significantly different than that in un-treated cells, while the O-GlcNAc levels in PUGNAc and STZ-treated cells notably increased. This indicates that Compounds 1 and 3 exhibited lower inhibitory effects on human β-GlcNAcase as compared to PUGNAc and STZ.

Example 7

Targeting Hex B with Compound 5 in a 293T Cell Line Expressing Hex B

A DNA fragment encoding human Hex B was amplified by PCR and cloned into pCMV-Tag 2B vector (Stratagene) to produce FLAG-tagged HexB expression plasmid (pFLAG-HexB). This plasmid was introduced into 293T cells to establish a cell line stably expressing FLAG-HexB. Briefly, 293T cells were maintained in Dulbecco's modified Eagle's medium (DMEM) supplemented with 10% (by volumn) heat inactivated fetal bovine serum (FBS), 2 mM glutamine, 100 units/mL penicillin and 100 $\mu$g/mL streptomycin at 37° C. in a 5% $CO_2$ atmosphere. These cells were transfected with expression plasmid pFLAG-HexB and plasmid pBabe-puro (carrying a puromycin resistance gene) at a molar ratio of 30-40:1. 8 hours later, the transfected cells were fed with fresh medium and incubated for 16 h. These cells were then cultured in puromycin-containing (2 $\mu$g/mL) medium for 2-3 weeks to screen for puromycin-resistant clones. A cell line, 293T/FLAG-HexB, selected from the just-noted screening process, was found to stably express FLAG-HexB at a high level.

Binding of Compound 5 to HexB was first examined by in situ immunostaining as follows. 293T/FLAG-HexB cells were grown on glass coverslips in the presence of biotin-conjugated Compound 5 and fixed in 4% paraformaldehyde for 15 min. The fixed cells were washed with PBS with 0.5% Triton-X100 and then stained with (1) 4',6'-diamidino-2-phenylindole (DAPI) to detect nuclei, (2) a mouse anti-FLAG antibody (M2, Sigma) and goat anti-mouse Alexa Fluor 594 (an anti-mouse IgG antibody from Invitrogen), or (3) a rabbit anti-biotin antibody (Abcam, Sigma) and goat anti-rabbit Alexa Fluor 488 (an antibody specific to rabbit IgG provided by Invitrogen). The coverslip were then mounted with Prolong antifade reagent (Molecular Probes) and signals released from each fluorescent dye were examined under Leica TCS SP2 Confocal Microscopec and Incubation System (Leica, Germany). Results thus obtained indicate that FLAG-HexB and Compound 5 were co-localized in the cytoplasm of the 293T/FLAG-HexB cells, indicating that Compound 5 bound to HexB in cells.

Binding of Compound 5 to FLAG-HexB were further confirmed by immuno-precipitation and Westernblot assays. The 293T/FLAG-HexB cells were lysed with a lysis buffer containing 1% NP-40, 10 mM Tris-HCl at pH 7.4, 150 mM NaCl, 2 mM EDTA, 1 mM phenylmethylsulfonyl fluoride, and a proteinase inhibitor cocktail (Sigma), and the cell lysate was then incubated at room temperature for 10 min in the presence or absence of Compound 5 (200 nM). Anti-FLAG antibody-sepharose beads or streptavidin-agarose beads were added to the cell lysate and the resultant mixtures were incubated at 4° C. for 1 h. These beads were collected and washed several times with the lysis buffer. Proteins attached to these beads were then eluted and subjected to westernblot analysis with the anti-FLAG antibody mentioned above. Results obtained from this study show that the FLAG-HexB protein was attached to the streptavidin-agarose beads, indicating that this protein is associated with the biotin-conjugated Compound 5.

Example 8

Effect of Compound 5 on GM2 Ganglioside Accumulation in Microglia Cells

BV2 cells (mouse microglia cells) were cultured in DMEM for 24 hr in 60-mm tissue culture dishes. The cells were washed once with PBS (pH 7.4), and 2 mL of fresh medium with or without biotin conjugated Compound 5 (at different concentrations) was added to each dish. After being incubated in a 5% $CO_2$ incubator at 37° C. for 16 hr, the BV2 cells were harvested, re-suspended in a solution containing PBS and 2×SDS lysis buffer (250 mM Tris, pH 6.8/4% SDS/20% glycerol/0.002% bromophenol blue/10% 2-mercaptoethanol) at a ratio of 1:1 to produce whole cell lysates. The cell lysates were boiled and then subjected to SDS-PAGE (15%) using a mini-gel apparatus (Biorad, Germany). Substances contained in the gel were transferred to a nitrocellulose membrane (Millipore) at 1 mA/cm² using a semidry blot system (Biorad, Germany). The membrane was blocked with a Tris-buffered saline (TBST) (50 mM Tris-HCl, pH 7.5; 150 mM NaCl; 0.1% Tween-20) containing 5% skim-milk and then blotted with an anti-Ganglioside asialo GM2 antibody and an anti-GAPDH antibody. Results obtained from this study show that ganglioside GM2 accumulated in Compound 5-treated BV2 cells in a dose-dependent manner.

The accumulation of ganglioside GM2 in microglia cells was further confirmed by an in situ immunostaining assay as described in Example X above, using antibodies against GM2 and biotin.

Additionally, BV2 cells were treated with Compound 3 (200 nM), Compound ix (200 nM), or PUGNAc (200 nM) for 10 days. Glycosphingolipids (e.g., GM2) were extracted from the treated cells with chloroform/methanol and the ganglioside levels were determined by high performance thin-layer chromatography. The results show that the GM2 level in Compound 3-treated cells significantly increased, while the GM2 levels in Compound ix and PUGNAc-treated cells only modestly increased. This indicates that Compound 3 is much more effective in increasing GM2 ganglioside accumulation than Compound ix and PUGNAc.

Taken together, the results discussed above demonstrate that Compounds 3 and 5 successfully modulated the intracellular GM2 levels in microglia cells.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound of formula (I):

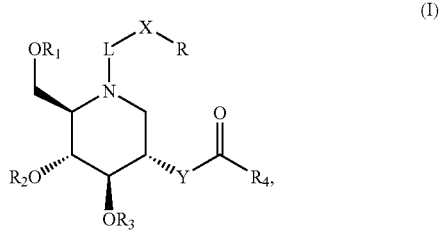

wherein
  L is —$(CH_2)_6$— or —$(CH_2)_7$—;
  X is —O—, —$NR_a$—, —NH—C(O)—, or deleted, in which $R_a$ is H, $C_{1-10}$ alkyl, aryl, heteroaryl, $C_{3-8}$ cycloalkyl, or $C_{1-7}$ heterocycloalkyl;
  R is $C_{1-10}$ alkyl, $C_{2-10}$ alkenyl, $C_{2-10}$ alkynyl, aryl, heteroaryl, $C_{3-8}$ cycloalkyl, or $C_{1-7}$ heterocycloalkyl, optionally substituted with $C_{1-10}$ alkyl, aryl, heteroaryl, $C_{3-8}$ cycloalkyl, $C_{1-7}$ heterocycloalkyl, halo, —$N_3$, —CN, nitro, amino, hydroxy, alkoxy, alkylthio, alkylcarbonyl, alkylcarbonyloxy, alkylcarbonylamino, or aminocarbonyl;
  Y is $NR_b$, in which $R_b$ is H, $C_{1-10}$ alkyl, aryl, heteroaryl, $C_{3-8}$ cycloalkyl, or $C_{1-7}$ heterocycloalkyl;
  each of $R_1$, $R_2$ and $R_3$, independently, is H, $C_{1-10}$ alkyl, aryl, heteroaryl, $C_{3-8}$ cycloalkyl, $C_{1-7}$ heterocycloalkyl, or $COR_c$, in which $R_c$ is $C_{1-10}$ alkyl, aryl, heteroaryl, $C_{3-8}$ cycloalkyl, or $C_{1-7}$ heterocycloalkyl; and
  $R_4$ is H, —O—($C_1$-$C_{10}$ alkyl), $C_1$-$C_{10}$ alkyl, $C_{2-10}$ alkenyl, $C_{2-10}$ alkynyl, aryl, heteroaryl, $C_{3-8}$ cycloalkyl, or $C_{1-7}$ heterocycloalkyl.

2. The compound of claim 1, wherein Y is NH.

3. The compound of claim 1, wherein each of $R_1$, $R_2$ and $R_3$ is H.

4. The compound of claim 1, wherein $R_4$ is $CH_3$.

5. The compound of claim 1, wherein L is $(CH_2)_6$ or $(CH_2)_7$, X is —NH—, —NH—C(O)—, or deleted; and R is $C_{1-10}$ alkyl, $C_{2-10}$ alkenyl, $C_{2-10}$ alkynyl, aryl, heteroaryl, $C_{3-8}$ cycloalkyl, or $C_{1-7}$ heterocycloalkyl, optionally substituted with $C_{1-10}$ alkyl, aryl, heteroaryl, $C_{3-8}$ cycloalkyl, $C_{1-7}$ heterocycloalkyl, halo, —$N_3$, —CN, nitro, amino, hydroxy, alkoxy, alkylthio, alkylcarbonyl, alkylcarbonyloxy, alkylcarbonylamino, or aminocarbonyl.

6. The compound of claim 5, wherein Y is NH.

7. The compound of claim 6, wherein each of $R_1$, $R_2$ and $R_3$ is H.

8. The compound of claim 7, wherein $R_4$ is $CH_3$.

9. The compound of claim 1, wherein the compound is selected from the group consisting of:

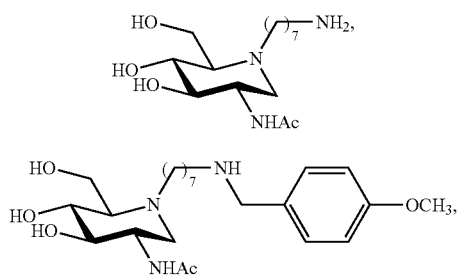

1

2

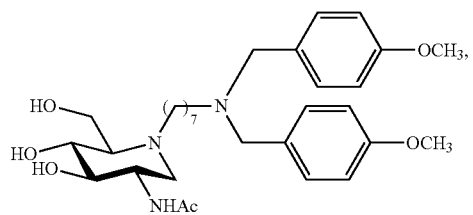

3

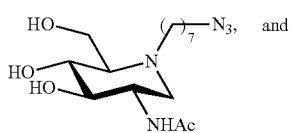

4

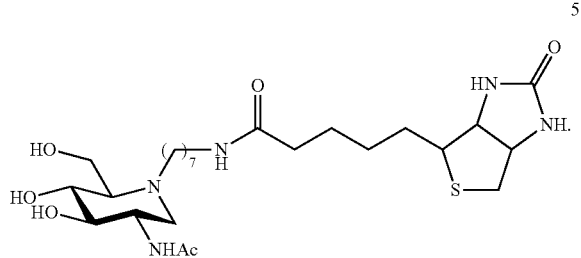

5

* * * * *